United States Patent
Marchese et al.

(10) Patent No.: US 7,179,494 B1
(45) Date of Patent: Feb. 20, 2007

(54) COMPOSITION AND METHOD FOR REDUCING INCIDENTS OF HOT FLASHES IN FEMALES

(75) Inventors: Frank P Marchese, Bronxville, NY (US); Harold Mermelstein, Bronx, NY (US); Paul Marchese, Bronxville, NY (US)

(73) Assignee: Marche Image Corp., Bronxville, NY (US)

( * ) Notice: Subject to any disclaimer, the term of this patent is extended or adjusted under 35 U.S.C. 154(b) by 0 days.

(21) Appl. No.: 11/335,989

(22) Filed: Jan. 20, 2006

(51) Int. Cl.
*A61K 36/00* (2006.01)

(52) U.S. Cl. ...................................... 424/725; 424/401

(58) Field of Classification Search ..................... None
See application file for complete search history.

(56) References Cited

U.S. PATENT DOCUMENTS

2003/0170325 A1* 9/2003 Mermelstein et al. ....... 424/729

* cited by examiner

*Primary Examiner*—Susan Hoffman

(57) ABSTRACT

A composition is provided for reducing incidents of hot flashes experienced by menopausal women, the composition comprising a mixture of water, a thickener, sorbitan monolaurate, cocoa butter or shea butter, polysorbate 20, dimethicone 200, bacteriacide, a pH adjuster and an effective amount of Chinese black cohosh. A method is also provided for preparing the composition and its use by menopausal women in need of treatment of hot flashes.

4 Claims, No Drawings

COMPOSITION AND METHOD FOR REDUCING INCIDENTS OF HOT FLASHES IN FEMALES

FIELD OF THE INVENTION

The present invention relates to a composition useful for reducing hot flashes experienced by females and is particularly related to a composition for substantially reducing or even eliminating incidents of hot flashes suffered by menopausal females. In one specific aspect this invention relates to such compositions which contain an aqueous extract of Chinese Black Cohosh. The present invention also relates to a method of applying these compositions to specific areas of the female body in order to realize reduction of incidents of hot flashes in such females.

BACKGROUND OF THE INVENTION

It is generally known that women upon attaining a certain age suffer menopausal and/or premenstrual symptoms which cause many discomforts and unpleasant side effects. These include vaginal dryness, pain and hot flashes, sweating and palpitations, all of which require medical attention and treatment. In U.S. Pat. No. 6,893,648 issued May 17, 2005 to Harold Mermelstein and Frank P. Marchese, the patentees disclose an herbal composition which alleviates vaginal dryness and pain associated with menopause and premenstrual symptoms. These compositions are used in gel form or in suppository form and can be applied topically to the affected area. The herbal compositions disclosed in the aforementioned patent include American Black Cohosh which is also known as Black Snakeroot, Bugbane Bugwort, *Cimicifuga*, Squawroot, Rattle Root and Rattle Weed. Its scientific name is *Cimicifuga Racemosa* from the family Ranunculaceae. The applicable parts are the rhizomiant root.

In a prior patent, i.e., U.S. Pat. No. 5,061,480 issued Oct. 29, 1991 to Frank P. Marchese and Joseph S. Eugenito, Jr., a composition is disclosed which is useful for tanning and skin treatment, which comprises specified non-ionic surfactants together with tyrosine, protein hydrolysate and riboflavin or adenosine triphosphate.

Scientific and medical knowledge nowadays indicate that hormones play a major role in producing physiological changes and activities in women. For instance, hormone imbalance of estrogen and progesterone can result in hot flashes, sweating and palpitations. Today estrogen replacement therapy offers some relief for women who suffer from these phenomena which are symptoms often associated with menopause. It is believed that during menopause the ovaries stop producing estrogen with a consequent reduction (imbalance) in the estrogen and progesterone in the system, thus resulting in the aforementioned undesirable symptoms. As far as it is known, there is no known composition today which can be used by females to find effective and long lasting relief from hot flashes and its associated undesirable symptoms during menopause.

It is therefore an object of the present invention to provide a composition which is effective in reducing or even substantially eliminating frequency of hot flashes experienced by females during menopause.

It is also an object of this invention to produce such compositions which can be self-applied by women without the need for assistance by others and without experiencing any discomfort.

It is a further object of the present invention to provide a method for self-application of such compositions by menopausal women to obtain the desired relief.

The foregoing and other objects of the present invention will be more fully appreciated from the ensuing detailed description and the clinical data obtained from application of the composition of this invention by women in menopausal state who are in need of relief from hot flashes and its associated symptoms.

SUMMARY OF THE INVENTION

The present invention provides a composition for reducing incidents of hot flashes experienced by women during or as a result of menopause. The composition comprises a mixture of a thickener, e.g., Ultrex 10 (polyacrylic acid), sorbitan monolaurate, either cocoa butter or shea butter, polysorbate 20, antibacterial agent and a pH adjuster, the balance being sterilized water, and an effective amount of water extract of Chinese black cohosh which contains formonocetin. The composition is prepared as a cream and is applied by the woman in need of treatment to her body, at an area between the belly button and the vagina, and rubbed gently, in the morning and at night. Clinical tests with this composition has demonstrated remarkable relief from, or reduction in incidents of hot flashes and some women have reported as high as 75 to 95 percent reduction in frequency of such incidents.

DETAILED DESCRIPTION OF THE INVENTION

In accordance with this invention a composition is provided which when applied by menopausal women to certain areas of their bodies, they experience relief from incidence of hot flashes and the pain and other unpleasant symptoms caused therefrom. The composition of this invention to be effective must include water extract of Asian (Chinese) Black Cohosh since this ingredient has been found to be essential for providing the needed relief. While some have used American Black Cohosh for this purpose, no real and lasting relief has been realized from compositions which contain American Black Cohosh. While not wishing to be bound by any particular theory, it is believed that water extract of Chinese Black Cohosh contains formonocetin which acts as the active ingredient, whereas the American Black Cohosh, or even alcohol extract of American Black Cohosh does not contain formonocetin and hence do not afford the needed relief.

Several compositions made according to the present invention were prepared and clinically tested to demonstrate their effectiveness. The following examples serve to illustrate the usefulness of these compositions.

EXAMPLE 1

2370 parts by weight of sterilized water was charged to a reaction vessel equipped with a stirrer, at room temperature. Thereafter 22 parts by weight of Ultrex 10, a polyacrylic acid thickener was added slowly to the reactor and mixed thoroughly with the water, followed by the addition of 15 parts by weight of ethylene diamine tetra acetic acid (EDTA) with continuous agitation resulting in Mixture A. Then, a separate mixture was formed in another reactor containing 277 parts by weight sorbitan monolaurate to which was added 83 parts by weight of polysorbate 20 (Tween®), 200 parts by weight of cocoa butter, 100 parts by weight of Dimethicone 200 having a viscosity of 700 cps, 10 parts by weight of methyl paraben, 5 parts by weight of ethyl paraben, and the mixture was heated thoroughly at 60° C. until a homogeneous mixture (Mixture B) was obtained. The two mixtures, i.e., Mixtures A and B, were mixed together under thorough agitation thereby forming a white oily mixture, Mixture C. To the resulting mixture C was then added, with continued agitation, at room temperature, 500 parts by weight of Collagen CLR, 250 parts by weight of Elastin and 250 parts of Unipertan 24 (lipobronze which contained tyrosine and adenine triphosphate) and 15 parts of Germal II, 550 parts by weight of water was added to the final mixture thereby forming a creamy composition. This composition had a pH of 6.4 and was divided into 50 gram portions and 287 milligrams (mg) of water extract of Chinese black cohosh dissolved in 10 cc of distilled water with anti-bacterial agent were added to each portion and mixed thoroughly for 15 minutes. The resulting creamy composition was clinically tested as described below. The ingredients in the composition of this example are listed below.

| | Ingredients | Parts by wt. | wt. % |
|---|---|---|---|
| 1. | sterilized water | 2888 | 62.25 |
| 2. | ULTREX X10 | 22 | 0.47 |
| 3. | tetrasodium EDTA | 15 | 0.32 |
| 4. | sorbitan monolaurate | 277 | 5.96 |
| 5. | cocoa butter | 200 | 4.30 |
| 6. | polysorbate 20 | 83 | 1.70 |
| 7. | dimethicone 200 | 100 | 2.15 |
| 8. | methyl paraben | 10 | 0.215 |
| 9. | propyl paraben | 5 | 0.107 |
| 10. | collagen (clear aqueous) Bovine | 500 | 10.76 |
| 11. | elastin (clear aqueous) | 250 | 5.38 |
| 12. | unipertan 242 (aqueous) | 250 | 5.38 |
| 13. | Germal II (50% aqueous) | 15 | 0.32 |
| 14. | sodium hydroxide (5% solution) | 10 | 0.215 |
| 15. | Chinese black cohosh | 22 | 0.473 |
| | TOTAL | 4647 | 100 |

Clinical Evaluation

Nineteen (19) women ranging in age between 48 and 53 participated voluntarily in the clinical evaluation. All of these women had reported significant incidents of hot flashes during and after menopause. The evaluation was carried out over five (5) weeks. During the first week there was no treatment, however, they all used the creamy composition prepared as in Example 1 during the next four (4) weeks and noted the incidents of hot flashes they experienced during this period. Each woman applied a small amount (thumb nail size) of the cream by smearing it across the lower part of the abdomen, between the navel and the vagina, every morning and before bed time, and each day they reported the results of the treatment. During the first week (without treatment) the women reported an average of 6.3 hot flashes per day. During the next four weeks (with treatment) the women reported 75–100 percent daily reduction in incidents of hot flashes. They also reported less problems with sleeping, less fatigue and less abnormal sweating. None reported any adverse effects.

When the same women applied a placebo (same composition but without the extract of Chinese black cohosh), only 20–30 percent reduction of incidents of hot flashes were reported. Thus, this example demonstrates the effectiveness of using extract of Chinese black cohosh in the composition.

EXAMPLE 2

In this example the ingredients in the composition and its preparation were basically the same as in Example 1 except that isopropanol extract of American black cohosh was used instead water extract of Chinese black cohosh. These ingredients are listed below:

| | Ingredients | Parts by wt. | wt. % |
|---|---|---|---|
| 1. | sterilized water | 2888 | 62.25 |
| 2. | ULTREX X10 | 22 | .47 |
| 3. | tetrasodium EDTA | 15 | .32 |
| 4. | sorbitan monolaurate | 277 | 5.96 |
| 5. | cocoa butter | 200 | 4.3 |
| 6. | polysorbate 20 | 83 | 1.7 |
| 7. | dimethicone 200 | 100 | 2.15 |
| 8. | methyl paraben | 10 | .215 |
| 9. | propyl paraben | 5 | .107 |
| 10. | collagen (clear aqueous) Bovine | 500 | 10.76 |
| 11. | elastin (clear aqueous) | 250 | 5.38 |
| 12. | unipertan 242 (aqueous) | 250 | 5.38 |
| 13. | Germal II (50% aqueous) | 15 | .32 |
| 14. | sodium hydroxide (5% solution) | 10 | .215 |
| 15. | American black cohosh | 22 | .473 |
| | TOTAL | 4647 | 100 |

Clinical Evaluation

The composition of Example 2 was clinically tested as in Example 1. Thirty five (35) women participated voluntarily whose ages ranged from 50 to 55. Each reported an average of 5 hot flashes per day during the first week (without treatment), and during the next four weeks, they reported only 20% reduction in experiencing incidents of hot flashes. They did also report less problems with sleeping and less abnormal sweating.

As it can be appreciated from the comparison of the clinical results of Examples 1 and 2, and with the placebo, the use of Chinese black cohosh in the composition drastically increases the efficacy of the composition as compared to compositions containing American black cohosh and that compositions containing American black cohosh are not significantly improved over the placebo.

While not wishing to be bound by any particular theory or mechanism, it is believed that the marked effectiveness of Chinese black cohosh containing composition is due to the presence of larger and hence effective amount of formonocetin, whereas the American black cohosh does not contain significant, if any, amount of formonocetin.

EXAMPLE 3

In this example the ingredients used were the same as in Example 1 except that it did not include Collagen, Elastin Unipertan, methyl paraben and propyl paraben. The ingredients and their amounts used are set forth below.

| | Ingredients | Parts by wt. | wt. % |
|---|---|---|---|
| 1. | sterilized water | 3883 | 83.5 |
| 2. | ULTREX X10 | 22 | .47 |
| 3. | tetrasodium EDAT | 15 | .32 |
| 4. | sorbitan monolaurate | 277 | 5.96 |
| 5. | shea butter | 211 | 4.466 |

-continued

| | Ingredients | Parts by wt. | wt. % |
|---|---|---|---|
| 6. | polysorbate 20 | 83 | 1.7 |
| 7. | dimethicone 200 | 100 | 2.15 |
| 8. | sodium benzoate | 10 | .215 |
| 9. | potassium sorbate | 10 | .215 |
| 10. | Germal II | 15 | .32 |
| 11. | triethanol amine (99%) | 10 | .215 |
| 12. | Chinese black cohosh | 22 | .47 |
| | TOTAL | 4658 | 100 |

The composition was prepared by first charging a reactor as in Example 1 with 2232 parts of distilled water followed by slowly adding 22 parts of Ultrex powder with continued stirring to form a thick mixture (Mixture A). Separately, Mixture B was formed by combining ingredients 4–7 in the stated amounts and heating to 55° C. This mixture was then added to Mixture A with agitation, and the resulting thick paste was mixed with 1567 parts distilled water with continued stirring. Thereafter 10 parts of sodium benzoate and 10 parts of potassium sorbate were added to the paste followed by addition of 15 parts of Germal II. The resulting creamy mixture was treated with 7 parts of 99% aqueous solution of triethanolamine giving a composition having a pH of 6.4.

300 mg. of water extract of Chinese black cohosh was added to several 50 gm-portions of the above composition and blended to produce a homogeneous cream.

Clinical Evaluation

Ten (10) women averaging in age between 48–53 participated in the clinical test. All these women had reported experiencing incidents of hot flashes 6 times per day. The clinical procedure which was followed was the same as hereinbefore described for Example 1. In the first week (without treatment) no reduction in hot flashes were reported. However, during the next four weeks (with treatment) 68% daily reduction n incidents of hot flashes was reported and 95% to 100% reduction was reported at the conclusion of four weeks of treatment. No sleeping problem was reported, and less fatigue and sweating were experienced.

When the same women were treated with placebo, no reduction in incidents of hot flashes were reported.

EXAMPLE 4

The composition prepared in this example was the same as in Example 3 using the same ingredients in the same amount and following the same procedure. However, the herb used was American black cohosh used in Example 1.

Clinical tests conducted on 7 women between of 51 and 55 in age, who had experienced 35 incidents of hot flashes per week. The test procedure was the same as in Example 3. No reduction in hot flashes was reported during the first week (without treatment) and only 28% reduction was reported at the conclusion of the clinical test period. Several reported some trouble with sleeping, but also reported less fatigue and less sweating.

When the same women were treated with placebo, no significant change was reported in experiencing incidents of hot flashes.

The Chinese black cohosh used herein refers to extract of the root of black cohosh plant which has been obtained by extraction with water. It is in the form of a brown powder and contains the active ingredient formonocetin. Extracts of the American black cohosh does not yield formonocetin and therefore compositions containing extracts of American black cohosh have not proven to be satisfactory for hot flash treatment.

The results of the foregoing examples and clinical evaluations indicate that effective and meaningful reduction in incidents of hot flashes are realized by the use of Chinese black cohosh. While these compositions have been prepared with specified amounts, the amount of the ingredients may vary somewhat without detracting from the effectiveness of the composition.

In the compositions described in the examples, methyl paraben, propyl paraben and germal II are used as the bactericide. One of more of these ingredients may be used in effective amount to provide the antibacterial effect required.

Also, as it can be noted from comparison of Examples 1 and 3, collagen, elastic and unipertan are used in Example 1 but not Example 3. These ingredients when included in the composition serve to improve the penetration of the composition cream into the skin and thus provide more effective relief. The compositions also include sodium hydroxide and/or tetrasodium EDTA to adjust the pH to the desired level, usually between about 6.2 to about 6.6, preferable about 6.4.

It must also be noted that many of the ingredients used herein are described in the aforementioned U.S. Pat. No. 5,061,480 and thus the disclosure of said patent is hereby incorporated by reference.

The invention claimed is:

1. A composition for reducing incidents of hot flashes experienced by menopausal women, said composition comprising, on weight percent basis, a mixture of from about 0.1 to about 2 percent thickener, from about 3 to about 8 percent sorbitan monolaurate, from about 1 to about 4 percent cocoa butter or shea butter, from about 1 to about 5 percent polysorbate 20, from about 1 to about 5 percent dimethicone 200, from about 0.1 to about 0.5 antibacterial agent, the balance being water, and further including from about 0.5 to about 5 percent of Chinese black cohosh based on weight of said mixture.

2. A composition as in claim 1 further containing from about 1 to 30 percent of a compound selected from the group consisting of collagen, elastin, unipertan and a mixture thereof.

3. A composition as in claim 1 further including an effective amount of a pH adjuster to adjust the final pH of said composition to about 6.2 to 6.6.

4. A composition as in claim 2 further including an effective amount of a pH adjuster to adjust the final pH of said composition to about 6.2 to 6.6.

\* \* \* \* \*